US012791483B2

(12) United States Patent
Ember et al.

(10) Patent No.: US 12,791,483 B2
(45) Date of Patent: Nov. 10, 2026

(54) METHODS AND SYSTEMS FOR INTERROGATING A DROP OF SALIVA USING RAMAN SPECTROSCOPY

(71) Applicants: VAL-CHUM, LIMITED PARTNERSHIP, Québec (CA); POLYVALOR, LIMITED PARTNERSHIP, Québec (CA)

(72) Inventors: Katie Ember, Montreal (CA); François Daoust, Pointe-Claire (CA); Nassim Ksantini, Montréal (CA); Fabien Picot, L'Houmeau (FR); Frédéric Leblond, Terrebonne (CA); Dominique Trudel, Montréal (CA)

(73) Assignee: CORPORATION DE L'ECOLE POLYTECHINIQUE DE MONTRÉAL, Montreal (CA)

( * ) Notice: Subject to any disclaimer, the term of this patent is extended or adjusted under 35 U.S.C. 154(b) by 155 days.

(21) Appl. No.: 18/571,038

(22) PCT Filed: Jun. 17, 2022

(86) PCT No.: PCT/CA2022/050974
§ 371 (c)(1),
(2) Date: Dec. 15, 2023

(87) PCT Pub. No.: WO2022/261781
PCT Pub. Date: Dec. 22, 2022

(65) Prior Publication Data

US 2024/0280491 A1 Aug. 22, 2024

Related U.S. Application Data

(60) Provisional application No. 63/212,327, filed on Jun. 18, 2021.

(51) Int. Cl.
*G01N 21/65* (2006.01)
*A61B 5/00* (2006.01)
*G01N 33/487* (2006.01)

(52) U.S. Cl.
CPC ........... *G01N 21/65* (2013.01); *A61B 5/0075* (2013.01); *A61B 5/4277* (2013.01); *G01N 33/487* (2013.01); *G01N 2201/1296* (2013.01)

(58) Field of Classification Search
CPC ................. G01N 21/65; G01N 33/487; G01N 2201/1296; A61B 5/0075; A61B 5/4277
See application file for complete search history.

(56) References Cited

U.S. PATENT DOCUMENTS

| | | | | |
|---|---|---|---|---|
| 11,337,611 B2 | 5/2022 | Fazlin et al. | | |
| 2004/0063214 A1* | 4/2004 | Berlin | G01N 21/65 356/301 | |

(Continued)

FOREIGN PATENT DOCUMENTS

| | | |
|---|---|---|
| CN | 105300954 A | 2/2016 |
| CN | 105388140 A | 3/2016 |

(Continued)

OTHER PUBLICATIONS

Radzol, A. R. M., Khuan Y. Lee, and Wahidah Mansor. "Nonstructural protein 1 characteristic peak from NS1-saliva mixture with surface-enhanced Raman spectroscopy." 2013 35th Annual International Conference of the IEEE Engineering in Medicine and Biology Society (EMBC). IEEE, 2013. (Year: 2013).*

(Continued)

*Primary Examiner* — Dominic J Bologna
(74) *Attorney, Agent, or Firm* — Norton Rose Fulbright Canada LLP; Reno Lessard

(57) ABSTRACT

There is described a method of interrogating saliva. The method generally having: receiving a drop of saliva on a
(Continued)

substrate; using a Raman spectroscopy measurement unit, performing a Raman spectroscopy measurement on the drop of saliva received on the substrate, said performing including interrogating said drop of saliva with a Raman excitation beam having a beam dimension greater than a given beam dimension threshold of about 0.1 mm, thereby simultaneously interrogating molecular content distributed in at least a given area of the drop of saliva, and generating at least a Raman spectrum resulting from said Raman spectroscopy measurement; and using a computer, accessing said Raman spectrum, comparing said Raman spectrum to reference data, and generating a signal based on said comparison.

20 Claims, 11 Drawing Sheets

(56) References Cited

U.S. PATENT DOCUMENTS

2004/0142484 A1* 7/2004 Berlin .................... G01N 21/65 436/171
2010/0291599 A1 11/2010 Tague, Jr. et al.
2011/0207622 A1* 8/2011 Wong ..................... C12Q 1/689 435/7.1
2012/0300201 A1 11/2012 Owen et al.
2014/0371450 A1 12/2014 Ren et al.
2017/0150949 A1* 6/2017 Lim ..................... G01N 33/487
2018/0136040 A1* 5/2018 Sodeoka ............... G01J 3/0221
2018/0238805 A1* 8/2018 Vinogradova ....... A61B 5/0075
2020/0319110 A1* 10/2020 Venegas Del Valle ...................... G01N 21/65
2021/0372933 A1* 12/2021 Xie ........................ G16H 40/63
2022/0381697 A1* 12/2022 Atkins .................. G06T 7/0012
2025/0277746 A1* 9/2025 LaChapelle ............. H01S 5/125

FOREIGN PATENT DOCUMENTS

CN 206270250 U 6/2017
CN 207020083 U 2/2018
CN 109253998 A 1/2019
JP 2006084261 A 3/2006
JP 2008203235 A 9/2008
WO 2019140305 A1 7/2019
WO 2021110939 A1 6/2021

OTHER PUBLICATIONS

Gooding Edward A et al., Fast, cheap and in control:spectral imaging with handheld devices, May 5, 2017, [Proceedings of SPIE ISSN 0277-786X vol. 10524], SPIE, US, vol. 10210, May 5, 2017 (May 5, 2017), pp. 102100E-102100E, XP060088611, DOI: 10.1117/12.2279886ISBN: 978-1-5106-1533-5, Proceedings of SPIE.
Radzol A R M et al., Nonstructural protein 1 characteristic peak from NS1-saliva mixture with Surface-Enhanced Raman spectroscopy, Jul. 3, 2013, 2013 34th Annual International Conference of the IEEE.
C. Carlomagno et al., COVID-19 salivary Raman fingerprint: innovative approach for the detection of current and past SARS-CoV-2 infections, Scientific Reports vol. 11, Article No. 4943 (2021).

* cited by examiner

METHODS AND SYSTEMS FOR INTERROGATING A DROP OF SALIVA USING RAMAN SPECTROSCOPY

FIELD

The improvements generally relate to Raman spectroscopy and more specifically relate to the Raman spectroscopy for medical condition assessment purposes.

BACKGROUND

Raman spectroscopy is a spectroscopic technique which can be used to characterize atoms or molecules of a sample. In this technique, the sample is illuminated with a Raman excitation beam, generally comprising monochromatic photons, which excites vibrational, rotational, and/or other low-frequency modes of the atoms or molecules of the sample in a manner which causes them to scatter photons having a different energy level than those of the incident monochromatic photons. The shift(s) in the energy level(s) between the incident photons and the scattered photos give(s) signature information which can be used to characterize the atoms or molecules of the sample.

It is known that Raman spectroscopy can be used in the medical field to determine whether a biological sample contains healthy or unhealthy bodily tissues based on the respective signature information of such tissue. In these fields, a Raman excitation beam is generally focused on a point of the sample, from which Raman signal is collected to determine whether, at that point, the sample is healthy or unhealthy, a technique often referred to as "single-point Raman spectroscopy."

Although existing single-point Raman spectroscopy measurements are satisfactory to a certain degree, there remains room for improvement.

SUMMARY

It was found that there was a need in the industry for Raman spectroscopy measurements systems and methods aimed at interrogating saliva samples. The systems and methods disclosed therein go beyond single-point Raman spectroscopy measurements by interrogating, simultaneously or sequentially, a plurality of points of the drop of saliva. For instance, in some embodiments, the Raman excitation beam used in the Raman spectroscopy measurement is large enough to encompass a substantial area of the drop of saliva. Such Raman spectroscopic measurements can be said to be macroscopic as the Raman excitation beam interrogates simultaneously a macroscopic region comprising a plurality of points of the drop of saliva. When the drop of saliva is wet, it may be deposited into a suitably sized and shaped well which can confine the drop of saliva in a way that the molecular content of the saliva is homogeneously distributed within the well. In these embodiments, the macroscopic Raman excitation beam may encompass a substantial portion of the well, thereby simultaneously interrogating several points thereof. In other embodiments, the drop of saliva can be dried on a planar substrate, for instance, which typically produces a circular profile having a center region surrounded by an edge region, with crystalline elements and non-crystalline elements. In these latter embodiments, the dried drop of saliva can be interrogated as a whole using a macroscopic Raman excitation beam. In some other embodiments, the dried drop of saliva is instead interrogated using a smaller, microscopic Raman excitation beam. These smaller measurements can be performed simultaneously or sequentially at at least two spaced apart points of the drop of saliva, including a first region encompassing crystalline elements and a second region encompassing non-crystalline elements where different form and structure indicative of a different molecular content can be found.

As will be described in further detail below, the methods and systems described herein involve the interrogation of saliva samples using Raman spectroscopic measurement(s). In some embodiments, the methods and systems described herein also involve the use of reference data which typically include a plurality of reference Raman spectra associated to a plurality of different medical conditions including, but not limited to, COVID-19 positive or negative, smoker or non-smoker, cancerous or healthy, respiratory disease(s), diabetes, heart disease(s), dental disease(s), sexually transmitted infection(s), viral hepatitis, vitamin deficiencies, mineral deficiencies and the like. Accordingly, by performing one or Raman spectroscopy measurements on a drop of saliva using either the macroscopic or microscopic Raman interrogation beam, and by comparing the resulting Raman spectra to corresponding reference Raman spectra of the reference data, the methods and systems described herein can determine whether one or more medical conditions can be associated to the interrogated drop of saliva.

In accordance with a first aspect of the present disclosure, there is provided a method of interrogating saliva, the method comprising: receiving a drop of saliva on a substrate; using a Raman spectroscopy measurement unit, performing a Raman spectroscopy measurement on the drop of saliva received on the substrate, said performing including interrogating said drop of saliva with a Raman excitation beam having a beam dimension greater than a given beam dimension threshold of about 0.1 mm, thereby simultaneously interrogating molecular content distributed in at least a given area of the drop of saliva, and generating at least a Raman spectrum resulting from said Raman spectroscopy measurement; and using a computer, accessing said Raman spectrum, comparing said Raman spectrum to reference data, and generating a signal based on said comparison.

Further in accordance with the first aspect of the present disclosure, the drop of saliva can for example be a drop of processed saliva.

Still further in accordance with the first aspect of the present disclosure, the substrate can for example have a well, said receiving including receiving the drop of saliva within the well, the well having a floor surface and an internal wall surface protruding from said floor surface, the floor surface and at least a portion of the internal wall surface confining the drop of saliva therewithin, the confined drop of saliva having molecular content being homogeneously distributed across the well.

Still further in accordance with the first aspect of the present disclosure, said performing can for example include interrogating at least a portion of the homogeneously distributed molecular content of the confined drop of saliva confined within the well.

Still further in accordance with the first aspect of the present disclosure, said receiving can for example include drying the drop of saliva.

Still further in accordance with the first aspect of the present disclosure, said substrate can for example be a planar substrate, said receiving including depositing a drop of saliva on the planar substrate.

Still further in accordance with the first aspect of the present disclosure, the method can for example further comprise drying the drop of saliva deposited on the planar substrate, the drop of saliva drying into a circular profile having a center region surrounded by an edge region, with crystalline elements and non-crystalline elements.

Still further in accordance with the first aspect of the present disclosure, said performing can for example include simultaneously interrogating at least some of the crystalline elements and at least some of the non-crystalline elements of the dried drop of saliva received on the planar substrate.

Still further in accordance with the first aspect of the present disclosure, the beam dimension threshold can for example be between about 0.1 mm and about 10 mm, preferably between about 0.5 mm and about 5 mm, and most preferably between about 1 mm and about 2 mm.

Still further in accordance with the first aspect of the present disclosure, the Raman excitation beam can for example simultaneously encompass at least a portion of a center region and at least a portion of an edge region of the drop of saliva.

Still further in accordance with the first aspect of the present disclosure, said interrogating can for example include the Raman excitation beam encompassing an entirety of the drop of saliva.

Still further in accordance with the first aspect of the present disclosure, said reference data can for example include a reference Raman spectrum associated to a medical condition, said comparing including comparing the Raman spectrum to the reference Raman spectrum, and determining whether the medical condition is present in the drop of saliva based on said comparing.

Still further in accordance with the first aspect of the present disclosure, said comparing can for example include comparing Raman emission content present within a given spectral region of the Raman spectrum to reference Raman emission content present within the given spectral region of the reference Raman spectrum.

Still further in accordance with the first aspect of the present disclosure, said medical condition can for example be COVID-19 positive, the given spectral region extends between about 300 $cm^{-1}$ and about 3500 $cm^{-1}$.

Still further in accordance with the first aspect of the present disclosure, the drop of saliva can for example have a volume ranging between about 0.5 μL and 100 μL, preferably between about 1 μL and 50 μL and most preferably between about 1 μL and 10 μL.

In accordance with a second aspect of the present disclosure, there is provided a Raman spectroscopy system for interrogating saliva, the Raman spectroscopy system comprising: a substrate receiving a drop of saliva; a Raman spectroscopy measurement unit configured for performing a Raman spectroscopy measurement on the drop of saliva received on the substrate, said performing including interrogating said drop of saliva with a Raman excitation beam having a beam dimension greater than a given beam dimension threshold of about 0.1 mm, thereby simultaneously interrogating molecular content distributed in at least a given area of the drop of saliva, and generating at least a Raman spectrum resulting from said Raman spectroscopy measurement; and a computer communicatively coupled to the Raman spectroscopy measurement unit, the computer having a processor and a memory having stored thereon instructions that when executed by the processor perform the steps of: accessing said Raman spectrum; comparing said Raman spectrum to reference data; and generating a signal based on said comparison.

Further in accordance with the second aspect of the present disclosure, the beam dimension threshold can for example be between about 0.1 mm and about 10 mm, preferably between about 0.5 mm and about 5 mm, and most preferably between about 1 mm and about 2 mm.

Still further in accordance with the second aspect of the present disclosure, the substrate can for example have a well, the well having a floor surface and an internal wall surface protruding from said floor surface, the floor surface and at least a portion of the internal wall surface confining the drop of saliva therein, the confined drop of saliva having molecular content being homogeneously distributed across the well.

Still further in accordance with the second aspect of the present disclosure, said performing can for example include interrogating at least a portion of the homogeneously distributed molecular content of the confined drop of saliva confined within the well.

Still further in accordance with the second aspect of the present disclosure, at least the floor surface and the internal wall surface of the well can for example be made of aluminum.

Still further in accordance with the second aspect of the present disclosure, the well can for example have a cross-sectional area smaller than 80 $mm^2$, preferably smaller than 15 $mm^2$ and most preferably smaller than 3 $mm^2$.

Still further in accordance with the second aspect of the present disclosure, the well can for example have a depth below about 50 mm, preferably below 100 mm and most preferably below 3 mm.

Still further in accordance with the second aspect of the present disclosure, said substrate can for example be a planar substrate onto which the drop of saliva is deposited and dried, the dried drop of saliva having a circular profile having a center region surrounded by an edge region, with crystalline elements and non-crystalline elements.

Still further in accordance with the second aspect of the present disclosure, said performing can for example include simultaneously interrogating at least some of the crystalline elements and at least some of the non-crystalline elements of the dried drop of saliva received on the planar substrate.

In accordance with a third aspect of the present disclosure, there is provided a method of interrogating saliva, the method comprising: receiving a drop of saliva on a substrate; drying the drop of saliva on the substrate, the dried drop of saliva having a circular profile having a center region surrounded by an edge region, with crystalline elements and non-crystalline elements; using a Raman spectroscopy measurement unit, performing first and second Raman spectroscopy measurements on the drop of saliva received on the substrate, the first Raman spectroscopy measurement including interrogating said drop of saliva with a Raman excitation beam focused on a first region of the dried drop of saliva, and generating a first Raman spectrum resulting from the first Raman spectroscopy measurement, the second Raman spectroscopy measurement including interrogating said drop of saliva with a Raman excitation beam focused on a second region of the dried drop of saliva, and generating a second Raman spectrum resulting from the first Raman spectroscopy measurement, the first and second regions being spaced apart from one another and containing different form and structure indicative of a different molecular content; and using a computer, accessing said first and second Raman spectra, comparing said first and second Raman spectra to reference data, and generating a signal based on said comparison.

Further in accordance with the third aspect of the present disclosure, the drop of saliva can for example be a drop of saliva supernatant.

Still further in accordance with the third aspect of the present disclosure, said first region can for example encompass at least some crystalline elements and the second region encompasses at least some non-crystalline elements of the dried drop of saliva.

Still further in accordance with the third aspect of the present disclosure, the first region can for example correspond to the center region of the circular profile of the dried drop of saliva and the second region corresponds to the edge region of the circular profile of the dried drop of saliva.

Still further in accordance with the third aspect of the present disclosure, said comparing can for example include comparing the first and second Raman spectra to first and second reference Raman spectra of the reference data.

Still further in accordance with the third aspect of the present disclosure, said substrate can for example be a planar substrate, said receiving including depositing a drop of saliva on the planar substrate.

Still further in accordance with the third aspect of the present disclosure, said first and second Raman spectroscopy measurements can for example be made sequentially to one another.

Still further in accordance with the third aspect of the present disclosure, the first and second Raman spectroscopy measurements can for example involve a Raman excitation beam having a beam dimension below a beam dimension threshold, the beam dimension threshold being between about 1 μm and about 50 μm, preferably about 2 μm and about 25 μm, and most preferably about 5 μm and about 10 μm.

Still further in accordance with the third aspect of the present disclosure, the reference data can for example include first and second reference Raman spectra associated to a medical condition, said comparing including comparing the first and second Raman spectra to the first and second reference Raman spectra, and determining whether the medical condition is present in the drop of saliva based on said comparing.

Still further in accordance with the third aspect of the present disclosure, said comparing can for example include comparing Raman emission content present within at least some given spectral regions of the first and second Raman spectra to reference Raman emission content present within the same at least some given spectral regions of the first and second reference Raman spectra.

Still further in accordance with the third aspect of the present disclosure, said medical condition can for example be COVID-19 positive, at least one of the given spectral regions extending between about 300 $cm^{-1}$ and about 3500 $cm^{-1}$.

Still further in accordance with the third aspect of the present disclosure, the drop of saliva can for example have a volume ranging between about 0.5 μL and 100 μL, preferably between about 1 μL and 50 μL and most preferably between about 1 μL and 10 μL.

In accordance with a fourth aspect of the present disclosure, there is provided a Raman spectroscopy system for interrogating saliva, the Raman spectroscopy system comprising: a substrate receiving a drop of saliva; a Raman spectroscopy measurement unit configured for performing first and second Raman spectroscopy measurements on the drop of saliva received in the substrate, the first Raman spectroscopy measurement including interrogating said drop of saliva with a Raman excitation beam focused on a first region of the dried drop of saliva, and generating a first Raman spectrum resulting from the first Raman spectroscopy measurement, the second Raman spectroscopy measurement including interrogating said drop of saliva with a Raman excitation beam focused on a second region of the dried drop of saliva, and generating a second Raman spectrum resulting from the first Raman spectroscopy measurement, the first and second regions being spaced apart from one another and containing different form and structure indicative of a different molecular content; and a computer communicatively coupled to the Raman spectroscopy measurement unit, the computer having a processor and a memory having stored thereon instructions that when executed by the processor perform the steps of: accessing the first and second Raman spectra; comparing said first and second Raman spectra to reference data; and generating a signal based on said comparison.

Further in accordance with the fourth aspect of the present disclosure, the first and second Raman spectroscopy measurements can for example involve a Raman excitation beam having a beam dimension below a beam dimension threshold, the beam dimension threshold being between about 1 μm and about 50 μm, preferably about 2 μm and about 25 μm, and most preferably about 5 μm and about 10 μm.

Still further in accordance with the fourth aspect of the present disclosure, the substrate can for example be made of aluminum.

Still further in accordance with the fourth aspect of the present disclosure, said first region can for example encompass at least some crystalline elements and the second region encompasses at least some non-crystalline elements of the dried drop of saliva.

Still further in accordance with the fourth aspect of the present disclosure, the first region can for example correspond to the center region of the circular profile of the dried drop of saliva supernatant and the second region corresponds to the edge region of the circular profile of the dried drop of saliva.

Still further in accordance with the fourth aspect of the present disclosure, said comparing can for example include comparing the first and second Raman spectra to first and second reference Raman spectra of the reference data.

Still further in accordance with the fourth aspect of the present disclosure, said substrate can for example be a planar substrate, said receiving including depositing a drop of saliva on the planar substrate.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
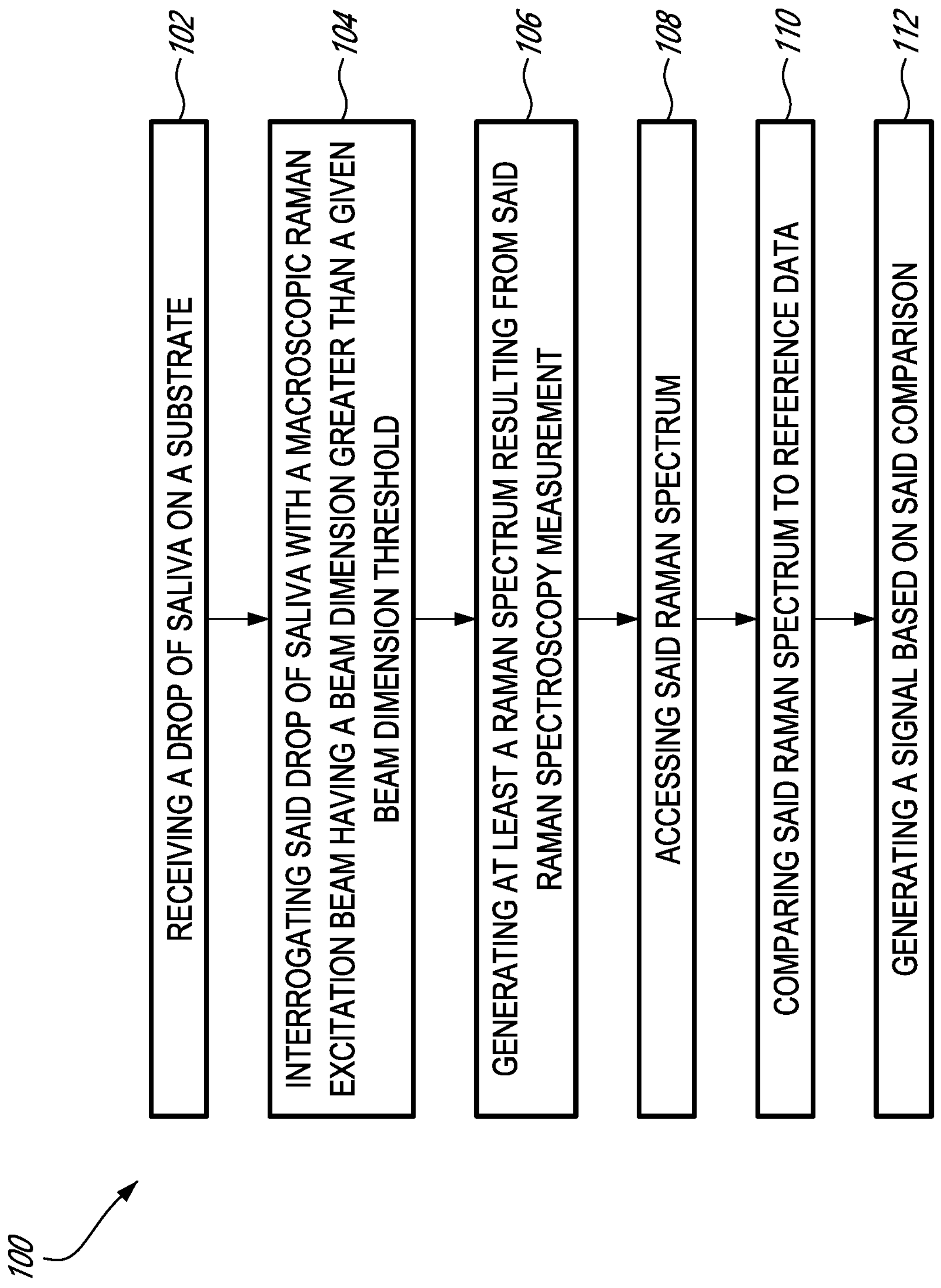
FIG. 1 is a flow chart of an example of a first method of interrogating saliva, involving a macroscopic Raman excitation beam, in accordance with one or more embodiments.

FIG. 1 shows a flow chart of an example of a method of interrogating saliva, in accordance with an embodiment.

At step 102, a drop of saliva is received on a substrate. It is intended that the received drop of saliva can either be a drop of raw saliva or a drop of processed saliva. In some embodiments, the drop of saliva is processed to provide a drop of saliva supernatant. As saliva samples typically tend to incorporate undesirable particles, it was found preferable in some embodiments to process the saliva samples into their constituents, including saliva solid pellets and saliva liquid supernatant, using a laboratory tabletop centrifuge, for instance, and performing measurements on the saliva supernatant alone. Once collected, the saliva supernatant can be stored into a sample container, frozen and kept at −80 degrees Celsius until measurements are made on the saliva supernatant. The drop of processed saliva may not be limited to saliva supernatant, for instance. In some embodiments, a saliva sample may be filtered to obtain a saliva filtrate which can also be stored into a sample container, frozen and kept at −80 degrees Celsius until measurements are made. The drop of processed saliva can also be provided in the form of a saliva fraction, which can result from the distilling of a saliva sample, for instance. Depending on the embodiment, it was found convenient to provide drops of saliva having a volume ranging between about 0.5 μL and 100 μL, preferably between about 1 μL and 50 μL and most preferably between about 1 μL and 10 μL. The volume of the drop of saliva can, of course, vary from one embodiment to another.

In some embodiments, the substrate onto which the drop of saliva is received is provided in the form of a planar substrate onto which the drop of saliva is deposited. In these embodiments, the drop of saliva may dry. The drying of the drop of saliva may result in a circular profile having a center region surrounded by an edge region, with crystalline elements and non-crystalline elements. In some other embodiments, the substrate includes a well inside which the drop of saliva may be received and contained, thereby homogeneously distributing the molecular content of the drop of saliva. Either way, the substrate can preferably be made of a material which is not or less susceptible to Raman emission upon Raman excitation. For instance, examples of such material can include, but are not limited to, aluminum, gold, silver, or any other metallic or electrically conductive material. In some embodiments, non-metallic substrates including, but not limited to, purified calcium fluoride ($CaF_2$), magnesium fluoride ($MgF_2$) and the like can be used.

At step 104, a Raman spectroscopy measurement is performed on the drop of saliva using a Raman spectroscopy measurement unit. The Raman spectroscopy measurement involves a step of interrogating the drop of saliva with a Raman excitation beam having a beam dimension greater than a given beam dimension threshold of about 0.1 mm. The beam dimension can for instance be a beam diameter measured at the intersection of the Raman excitation beam and the drop of saliva. A Raman excitation beam satisfying such a beam dimension threshold is often times referred to as a macroscopic Raman excitation beam in this disclosure. By doing so, a relatively substantial area of the drop of saliva is excited which in turn simultaneously interrogates a number of points of the molecular content of the drop of saliva. Depending on the embodiment, the beam dimension threshold can range between about 0.1 mm and about 10 mm, preferably between about 0.5 mm and about 5 mm, and most preferably between about 1 mm and about 2 mm.

At step 106, a Raman spectrum resulting from the Raman spectroscopy measurement is generated. The Raman spectrum can be generated in many ways. The Raman spectrum can be presented in the form of data representing an array or matrix of numbers or values, preferably showing a measurand indicative of a Raman emission intensity (e.g., such as an intensity value, a number of photon counts, SNR) as a function of a measurand indicative of spectral content or Raman shift. For instance, the Raman spectrum can include information showing intensity as a function of Raman shift. Such information may be referred to as a raw Raman spectrum. In some other embodiments, the generated Raman spectrum is processed to remove noise or some spectral information which is deemed to be irrelevant. Whether the generated Raman spectrum is raw or processed, the Raman spectrum can be stored on an accessible memory, communicated to an internal computer and/or shared to a remote computer via a wired or wireless communication protocol.

At step 108, the Raman spectrum is accessed by a computer. For instance, a computer can access the Raman spectrum via an accessible memory, from an internal computer and/or from a remote computer. At steps 110 and 112, the Raman spectrum is compared to reference data and a signal indicative of the comparison is generated.

In some embodiments, the reference data includes a reference Raman spectrum associated to a medical condition. In these embodiments, the comparing step includes comparing the Raman spectrum to the reference Raman spectrum, and determining whether the medical condition is present in the drop of saliva based on the comparison. The comparing step can involve a full comparison between the measured Raman spectrum and the reference Raman spectrum. However, in some other embodiments, the comparison can only be partial. In these latter embodiments, the comparing step includes the comparison of Raman emission content present within a given spectral region of the Raman spectrum to reference Raman emission content present within the given spectral region of the reference Raman spectrum. For instance, if it has been determined that Raman emission content present within a given spectral region is indicative of a particular medical condition, the comparing step can be limited to that given spectral region. In some embodiments, the given spectral region be a fingerprint region extending between about 300 $cm^{-1}$ and about 1900 $cm^{-1}$, a high wavenumber region extending between about 2400 $cm^{-1}$ and 3500 $cm^{-1}$, or both, depending on the embodiment. The spectral region can be expressed in terms of wavenumber units (e.g., in $cm^{-1}$), expressed in terms of a wavelength (e.g., in nm) and/or expressed in terms of a frequency (e.g., GHZ). However, it was found convenient to express the spectral region in terms of wavenumber units as this notation is independent of nanometers and excitation wavelength, for instance. This strategy can help enhance computational processing time. In this way, the computer may be able to determine whether the medical condition is present in the drop of saliva based on that partial comparison alone. There can be more than one spectral region of interest for any given medical condition in any given Raman spectra. In some specific embodiments, the medical condition to be assessed is COVID-19 positive. In this specific embodiment, this medical condition can be expressed by a reference Raman emission content having a signal-to-noise (SNR) ratio of at least about 3, preferably at least 4, and most preferably at least 5. In some embodiments, relative or normalized intensity is either above or below a corresponding intensity threshold. In some embodiments, the Raman emission content to be assessed is a ratio of a peak intensity value of the measured Raman spectrum to a peak intensity value of the reference Raman spectrum. Any type of difference or set of differences between the measured Raman emission spectra and the reference Raman emission spectra can be identified, and then be associated with a given medical condition, depending on the embodiment. In this embodiment, comparing the Raman emission content of the measured Raman spectrum to the reference Raman emission content can help determine whether the drop of saliva is COVID-19 positive. Other examples of assessable medical conditions can include, but are not limited to, COVID-19 positive or negative, smoker or non-smoker, cancerous or healthy, respiratory disease(s), diabetes, heart disease(s), dental disease(s), sexually transmitted infection(s), viral hepatitis, vitamin deficiencies, mineral deficiencies and the like. Such reference data can stem from reference measurements made onto real or synthetic reference saliva samples presenting a given medical condition. Preferably, the conditions under which the saliva sample of interest and the reference saliva samples are measured are similar, and the spectral regions inside which Raman emission content is to be compared are similar as well, thereby ensuring that any difference uncovered at the comparing step stem from a difference in the presence of the medical condition, for instance.

Figure 2:
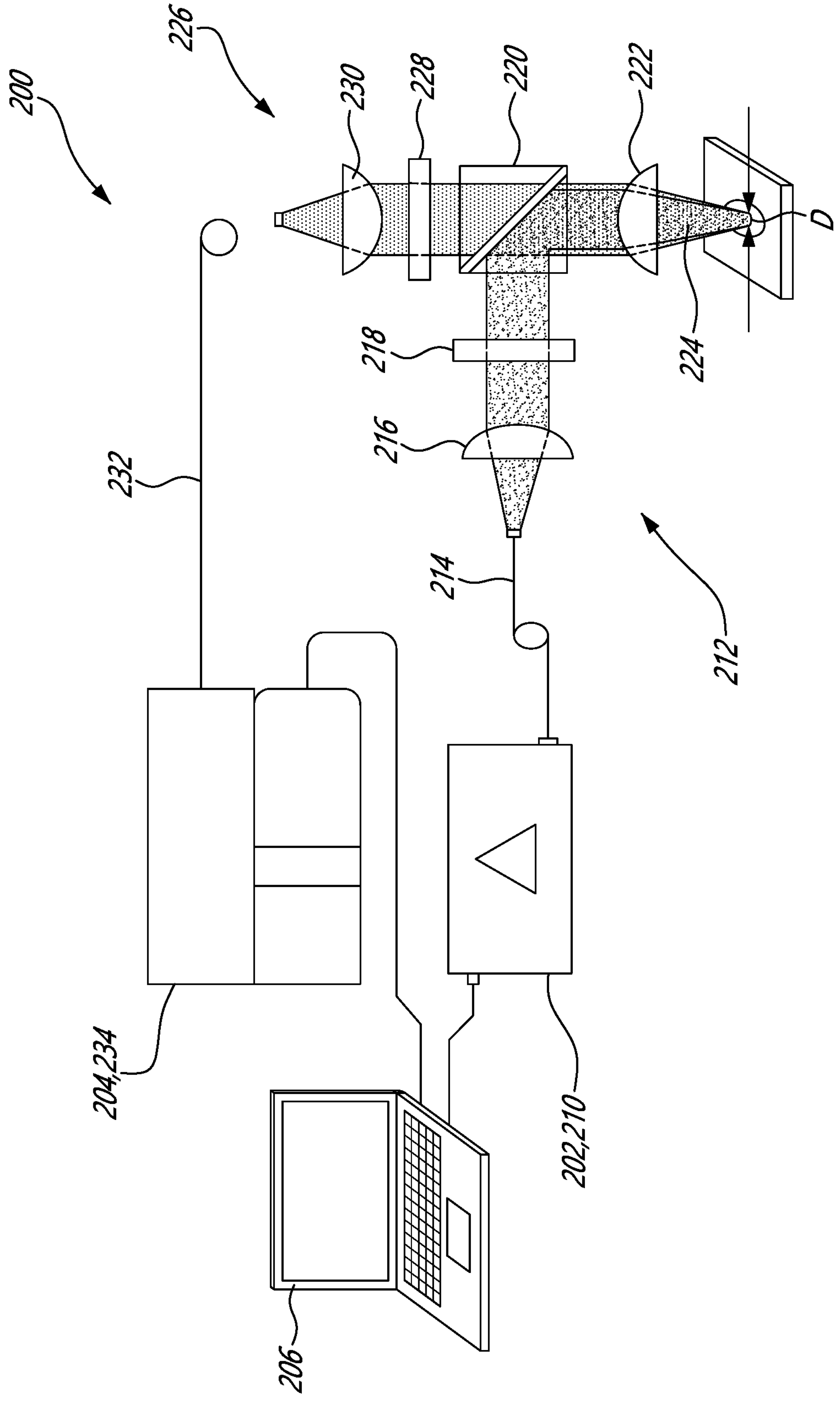
FIG. 2 is a schematic view of an example of a Raman spectroscopy measurement unit communicatively coupled to a computer, in accordance with one or more embodiments.

FIG. 2 shows an example of a Raman spectroscopy measurement unit 200, in accordance with an embodiment. In this embodiment, the Raman spectroscopy measurement unit 200 has a Raman excitation source 202 and a Raman emission detector 204 which are both communicatively coupled to a computer 206. As depicted, the coupling is wired in this embodiment. However, it is envisaged that the coupling can be wireless in some other embodiments. As shown, the Raman excitation source 202 is in this case provided in the form of a fibered laser source 210 operating at about 785 nm. The Raman spectroscopy measurement unit 200 includes a Raman interrogation path 212 having a fiber cable 214, a collimating lens 216, a band-pass filter 218, a dichroic mirror 220 and a focusing lens 222 providing a Raman excitation beam 224 having a required beam dimension D. A Raman emission path 226 is also shown. The Raman emission path 226 has the focusing lens 222, the dichroic mirror 220, a high-pass filter 228, an injection lens 230 and a fiber bundle 232 collecting as much of the Raman emission as possible and communicating it to the Raman emission detector 204. In this embodiment, the Raman emission detector 204 is provided in the form of a spectrometer 234. An example of such the fiber bundle 232 is described in PCT Patent Application Publication No. WO 2019/051,602 A1, the contents of which are hereby incorporated by reference. The use of the fiber bundle 232 has been found to be convenient as it can enhance the collected amount of Raman emission content. However, in some other embodiments the fiber bundle can only be optional as a standard Raman emission collecting fiber may be used. It is intended that the Raman spectroscopy unit described herein is meant to be exemplary only. Indeed, it is noted that other examples of Raman spectroscopy units can be used in some other embodiments. The optical components shown in this specific example are meant to be exemplary only, as in some other embodiments other optical components can equivalently be used. For instance, in this example some optical components are shared between the Raman interrogation path 212 and the Raman emission path 226. However, in some other embodiments, the optical components of the Raman interrogation and emission paths 212 and 226 are independent from one another.

Figure 3A:
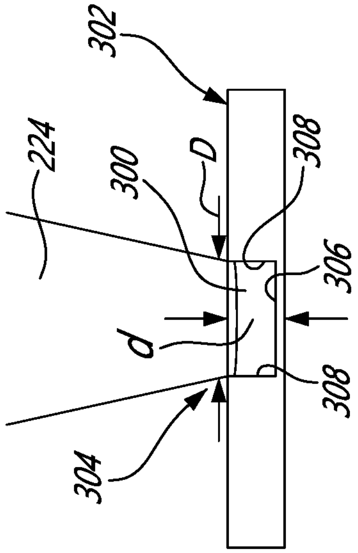
FIG. 3A is a sectional view of the substrate of FIG. 3, taken along section 3A-3A of FIG. 3, in accordance with one or more embodiments.
Figure 4:
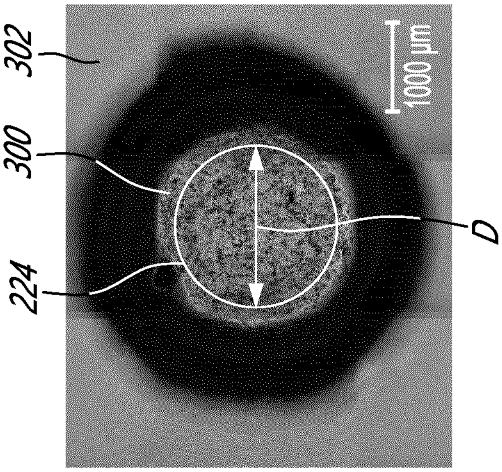
FIG. 4 is a top plan view of a wet drop of saliva received in the well of the substrate of FIG. 2, in accordance with one or more embodiments.
Figure 3:
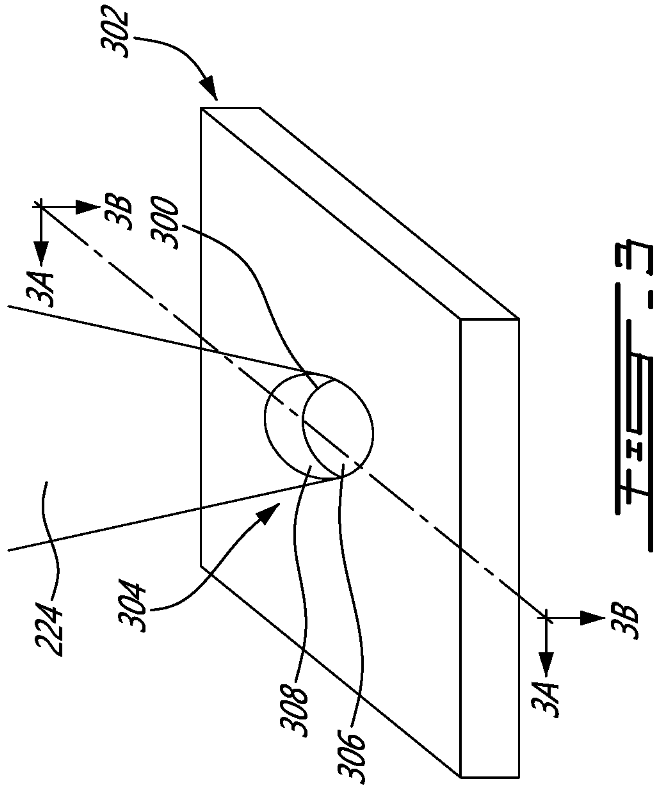
FIG. 3 is an oblique view of the substrate of FIG. 2, in accordance with one or more embodiments.
Figure 3B:
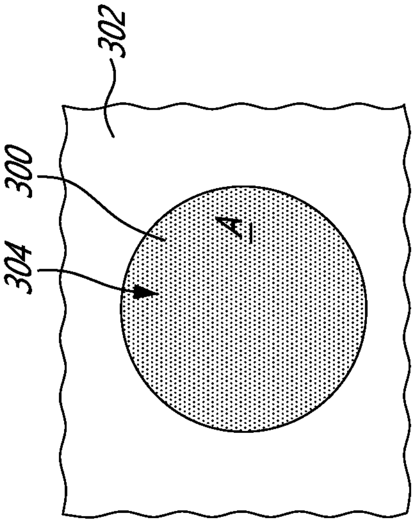
FIG. 3B is a sectional view of the substrate of FIG. 3, taken along section 3B-3B of FIG. 3, in accordance with one or more embodiments.

As best shown in FIGS. 3 and 3A, the Raman excitation beam 224 is focused onto a drop of saliva 300 received on a substrate 302, the substrate 302 used in this example is provided in the form of a well 304 having a floor surface 306 and an internal wall surface 308 protruding from the floor surface 306. A relationship between the volume of the drop of saliva 300 and the dimensions of the well 304 ensures that the drop of saliva 300 is suitably confined therewithin. Specifically, this relationship aims at confining the drop of saliva 300 within the well 304 in a way which, upon drying, will homogeneously distribute the saliva within the well 304. As shown in FIGS. 3A and 3B, it is believed that as soon as the volume of the drop of saliva 300 is such that it allows the saliva to touch a circumference of the internal wall surface 308 and form a meniscus, proper homogeneous distribution can be achieved. To achieve such a confinement, using a well 304 having a cross-sectional area A smaller than about 80 $mm^2$, preferably smaller than about 15 $mm^2$ and most preferably smaller than about 3 $mm^2$ was found convenient. The well can have a depth d below about 50 mm, preferably below 100 mm and most preferably below 3 mm. Using such a well can allow the Raman excitation beam to interrogate at least a portion of the homogeneously distributed molecular content of the confined drop of saliva 300, such as shown in FIG. 4. The cross-sectional area A of the well 304 is typically smaller than a diameter of a drop of saliva deposited on a planar substrate made from the same material than the well 304. The internal wall surface 308 of the well 304 thereby ensure confinement of the drop of saliva in a radially inward orientation as it dries. The depth of the well 304 is such that a volume of the well 304 is greater than or equal to a volume of the drop of saliva. As can be appreciated from this figure, the dimension D of the Raman excitation beam 224 encompass a substantial portion of the drop of saliva 300 in this example.

Figure 6:
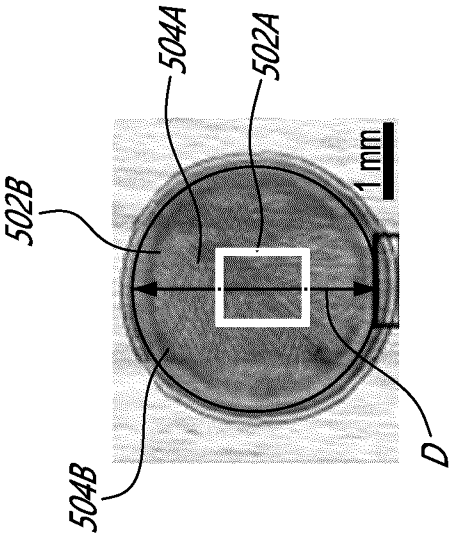
FIG. 6 is a top plan view of the dried drop of saliva received on the planar substrate of FIG. 5, in accordance with one or more embodiments.
Figure 5:
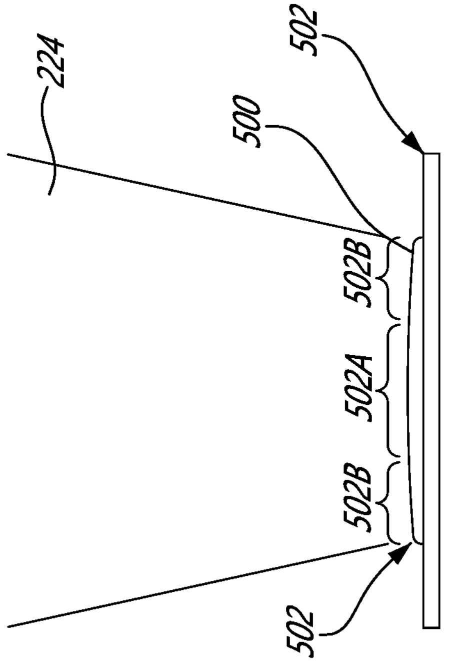
FIG. 5 is a side elevation view of an example of a planar substrate receiving a dried drop of saliva, in accordance with one or more embodiments.

In another embodiment, the Raman excitation beam 224 can be focused onto a drop of saliva 500 received on a planar substrate 502, such as shown in FIG. 5. Upon drying, the drop of saliva 500 dries into a circular profile 502 having a center region 502A surrounded by an edge region 502B, with crystalline elements and non-crystalline elements. In the depicted embodiment, the Raman excitation beam 224 encompasses an entirety of the drop of saliva 500. However, in some embodiments, the Raman excitation beam simultaneously encompasses at least a portion of a center region 502A and at least a portion of an edge region 502B of the drop of saliva 500. Typically, the crystalline elements 504A are distributed in the center region 502A whereas the non-crystalline elements 504B are distributed on the edge region 502B, such as shown in FIG. 6. Using a macroscopic Raman excitation beam having a beam dimension greater than a given threshold of about 0.1 mm allows the simultaneously interrogation of at least some of the crystalline elements 504*a* and at least some of the non-crystalline elements 504*b* of the dried drop of saliva 500 received on the planar substrate 502. Such an interrogation technique can be preferred in at least some embodiments.

As discussed above, whether the substrate is a well or a planar substrate, whether the drop is wholly or only partially interrogated by the macroscopic Raman excitation beam, it is intended that the reference Raman spectrum used in the comparison step performed by the computer should stem from similar measurement conditions including, but not limited to, similar ambient temperature, similar level of dryness of the drop of saliva, similar Raman excitation beam, similar beam dimension, similar beam intensity and the like.

The computer, such as the one described with reference to FIG. 2, can be provided as a combination of hardware and software components. The hardware components can be implemented in the form of a computing device 700, an example of which is described with reference to FIG. 7. Moreover, the software components of the computer can be implemented in the form of a software application 800, an example of which is described with reference to FIG. 8.

Figure 7:
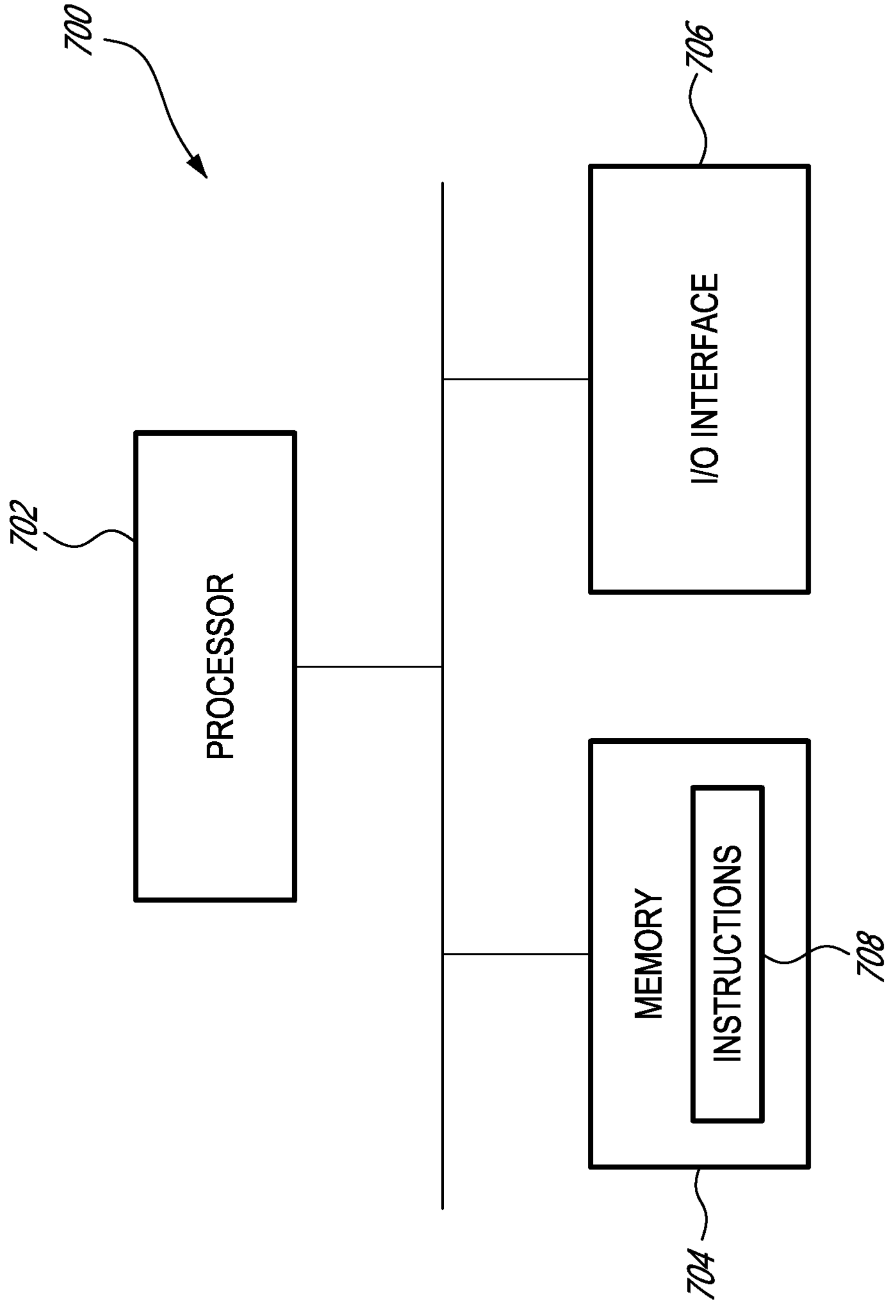
FIG. 7 is a block diagram of an example of a computing device of the computer of FIG. 2, in accordance with one or more embodiments.

Referring to FIG. 7, the computing device 700 can have a processor 702, a memory 704, and I/O interface 706. Instructions 708 to access the Raman spectrum, to compare the accessed Raman spectrum to reference data and to generate a corresponding signal for medical condition assessment can be stored on the memory 704 and accessible by the processor 702.

The processor 702 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 704 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 706 enables the computing device 700 to interconnect with one or more input devices, such as a mouse, a keyboard, an optical spectrometer and the like, or with one or more output devices such as a display, an external memory or network and a Raman excitation source.

Each I/O interface 706 enables the computer to communicate with other components, to exchange data with other components, to access and connect to network resources, to server applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 8:
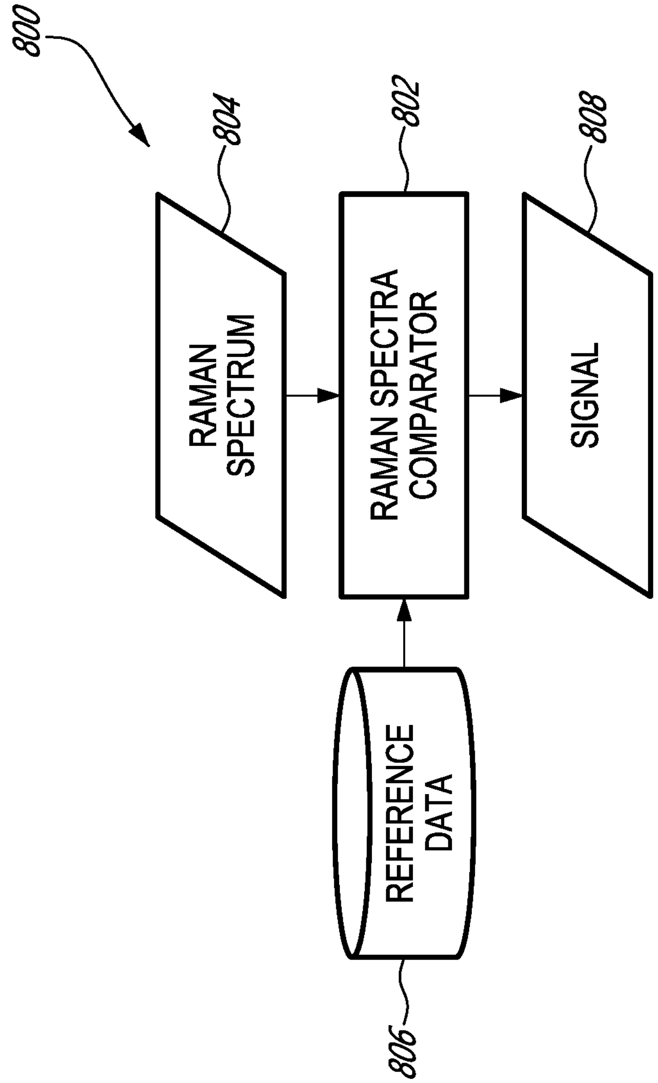
FIG. 8 is a block diagram of an example of a software application of the computer of FIG. 2, in accordance with one or more embodiments.

Referring now to FIG. 8, the software application 800 generally has a Raman spectra comparator 802 is configured to receive a Raman spectrum 804, to compare it to reference data 806 and to generate a signal 808 as per the instructions 708 stored on the memory 704 of the computing device 700. In some embodiments, the software application 800 is stored on the memory 704 and accessible by the processor 702 of the computing device 700.

In some embodiments, the Raman spectra comparator 802 can be trained using supervised learning. In such supervised learning, each training Raman spectrum in a set of training Raman spectra may be associated with a label indicative of a specific medical condition while training. Supervised machine learning engines can be based on Artificial Neural Networks (ANN), Support Vector Machines (SVM), capsule-based networks, Linear Discriminant Analysis (LDA), classification tree, a combination thereof, and any other suitable supervised machine learning engine. However, as can be understood, in some other embodiments, it is intended that the Raman spectra comparator 802 can be trained using unsupervised where only training Raman spectra are provided (no desired or truth outputs are given), so as to leave the trained Raman spectra comparator 802 find a structure or resemblances in the provided training Raman spectra. For instance, unsupervised clustering algorithms can be used. Additionally or alternately, the trained Raman spectra comparator 802 can involve reinforcement learning where the Raman spectra comparator 802 interact with example training Raman spectra and when they reach desired or truth outputs, the trained Raman spectra comparator 802 is provided feedback in terms of rewards or punishments. Two exemplary methods for improving classifier performance include boosting and bagging which involve using several classifiers together to "vote" for a final decision. Combination rules can include voting, decision trees, and linear and nonlinear combinations of classifier outputs. These approaches can also provide the ability to control the trade-off between precision and accuracy through changes in weights or thresholds. These methods can lend themselves to extension to large numbers of localized features. In any case, some Raman spectra comparator 802 may require human interaction during training, or to initiate the comparison, however human interaction may not be required while the comparison is being carried out, e.g., during analysis of an accessed Raman spectra. See Nasrabadi, Nasser M. "Pattern recognition and machine learning." Journal of electronic imaging 16.4 (2007): 049901 for further detail concerning such trained engines.

The computing device 700 and the software application 800 described above are meant to be examples only. Other suitable embodiments of the computer can also be provided, as it will be apparent to the skilled reader.

Figure 9A:
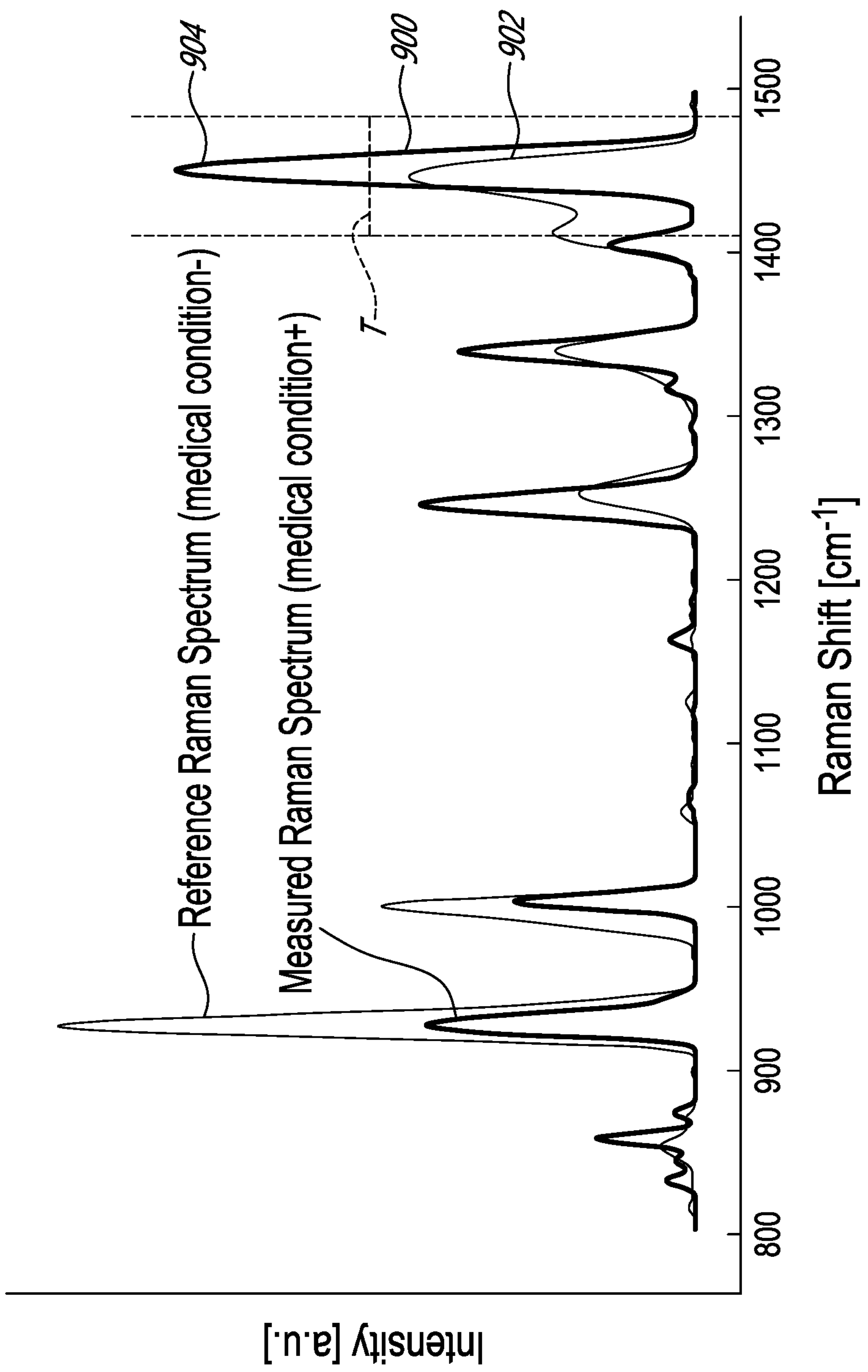
FIGS. 9A and 9B are graphs showing an example of a Raman spectrum resulting from a Raman spectroscopy measurement on the drop of saliva of FIG. 2, and corresponding reference Raman spectrum, in accordance with one or more embodiments.
Figure 9B:
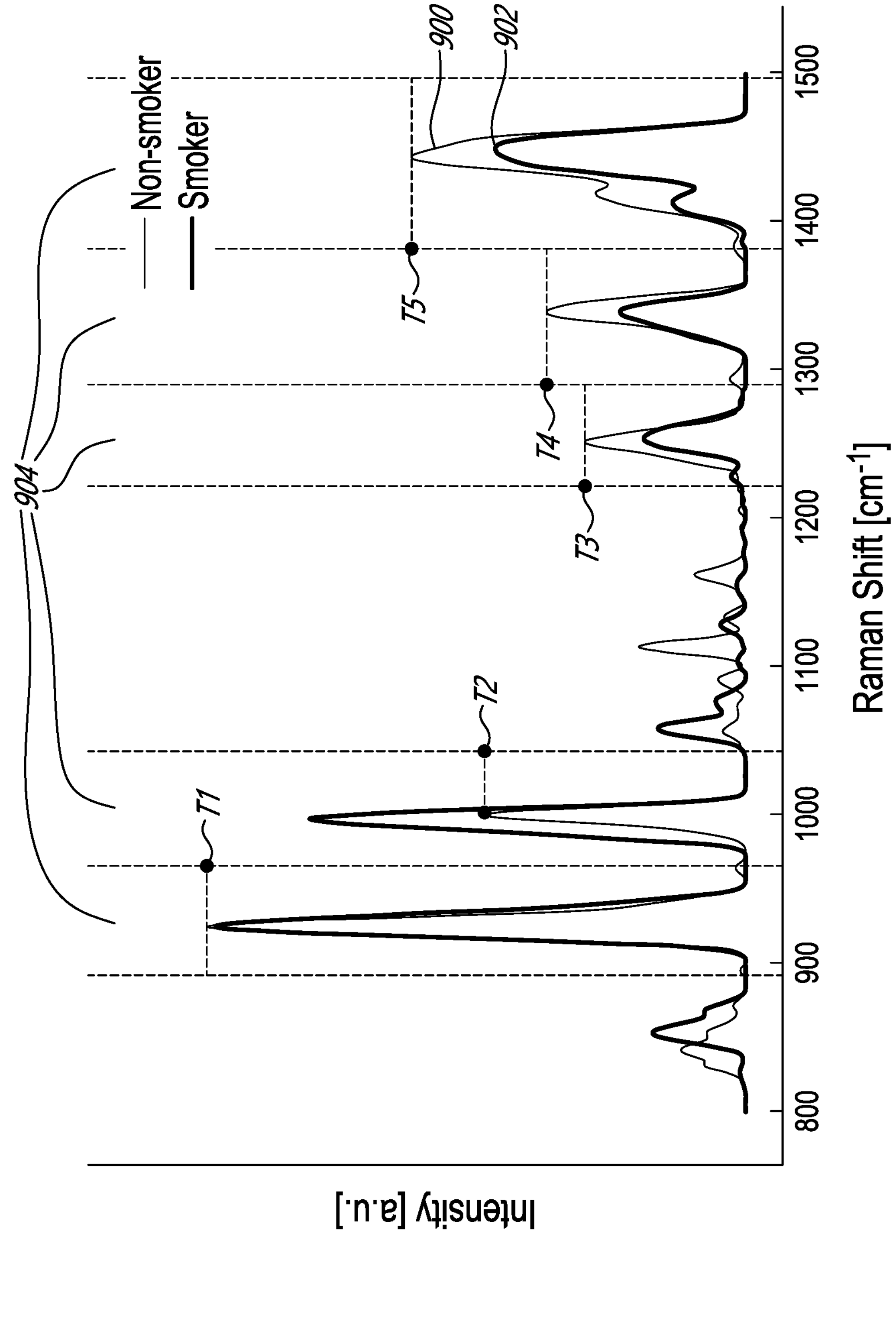

FIG. 9A shows an example of a measured Raman spectrum 900 and a reference Raman spectrum 902 both acquired under similar measurement conditions. In this example, both spectra 900 and 902 have been acquired upon a macroscopic Raman excitation. In this example, a given medical condition may be determined upon comparing the Raman emission content of a given spectral region 904 encompassing the 1450 nm peak. As such, one may determine that whenever a Raman emission content above a given threshold T is obtained in the given spectral region 904, the drop of saliva can be deemed to possess the medical condition. In this example, as the Raman emission content of the measured Raman spectrum 900 is above the threshold T in the given spectral region 904, the interrogated drop of saliva can be associated to the medical condition. Such a partial comparison can be used for some comparisons, however, some other comparisons may involve more than one spectral regions of interest and may involve the entirety of the Raman emission content for some conditions. For instance, FIG. 9B shows examples of a measured Raman spectrum 900 and a reference Raman spectrum 902 both acquired under similar measurement conditions. In this particular example, the reference Raman spectrum 902 is associated with a non-smoking medical condition whereas the measured Raman spectrum 900 is associated with a smoking medical condition. In this example, a number of different spectral regions 904 of the Raman spectra 900 and 902 may individually be compared to one another during the comparison step. In such an example, a plurality of thresholds T1 to T5 may be associated to each one of the spectral regions 904 for the comparison purposes. Other examples of comparison techniques can be used in some other examples.

Figure 10:
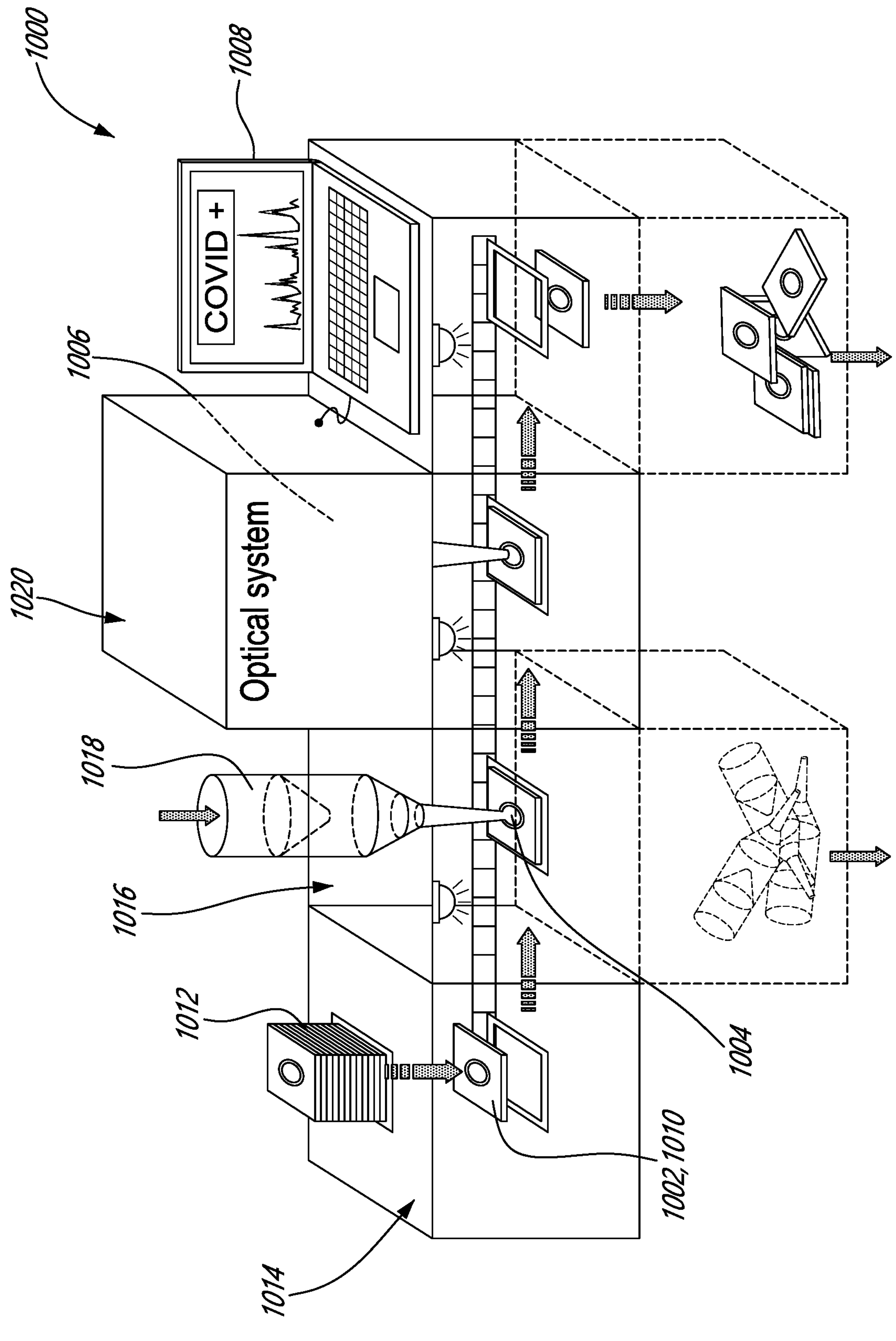
FIG. 10 is an oblique view of an example of an automated system for interrogating saliva, including a substrate provided in the form of a well, a Raman spectroscopy measurement unit, and a computer, in accordance with one or more embodiments.

FIG. 10 shows an example of an automated system 1000 for interrogating saliva, in accordance with a specific embodiment. As depicted, the system 1000 has a substrate 1002 receiving a drop of saliva 1004, a Raman spectroscopy measurement unit 1006 and a computer 1008 communicatively coupled to the Raman spectroscopy measurement unit 1006. In this specific embodiment, the substrate 1000 is provided in the form of a disposable well plate 1010 having a well such as discussed above. Disposable well plates can be moved among a plurality of stations to perform the Raman spectroscopy measurement in an automated manner. For instance, a stack 1012 of disposable well plates are made accessible to a sterilization station 1014 which is configured to shine ultraviolet light onto one of the disposable well plate 1010 at the time. The sterilized well plate 1010 can then be moved in a saliva collection station 1016 which is configured to deposit the drop of saliva 1004 into the well of the sterilized disposable well plate 1010. In this specific embodiment, a saliva filter 1018 is provided atop the saliva collection station 1016 such that saliva filtrate drips into the well of the sterilized well plate 1010. In some other embodiments, the drop of saliva can be deposited using a pipette which can be disposed thereafter in a disposal bin, for instance. The saliva containing disposable well plate 1010 is then moved in a Raman spectroscopy station 1020 incorporating the Raman spectroscopy measurement unit 1006 such as described above. Once a corresponding Raman spectrum is generated, the used well plate 1010 can be disposed in a disposal bin as well. As shown, the computer 1008 is communicatively coupled to the Raman spectroscopy measurement unit 1006 and can access the measured Raman spectrum, compare it to reference data made accessible to the computer 1008, and generate a signal indicative of the comparison. In this case, the signal can be used to display a medical condition assessment on a graphical user interface of the computer 1008. In this specific case, the medical condition assessment indicates that the interrogated drop of saliva is indeed COVID-19 positive. The well plate 1010 can be moved automatically using a conveyor mechanism moving the well plate 1010 along a path travelling across all of the stations of the system 1000. In some other embodiments, the conveyor is optional as the well plate 1010 may be manually moved between the stations.

Figure 11:
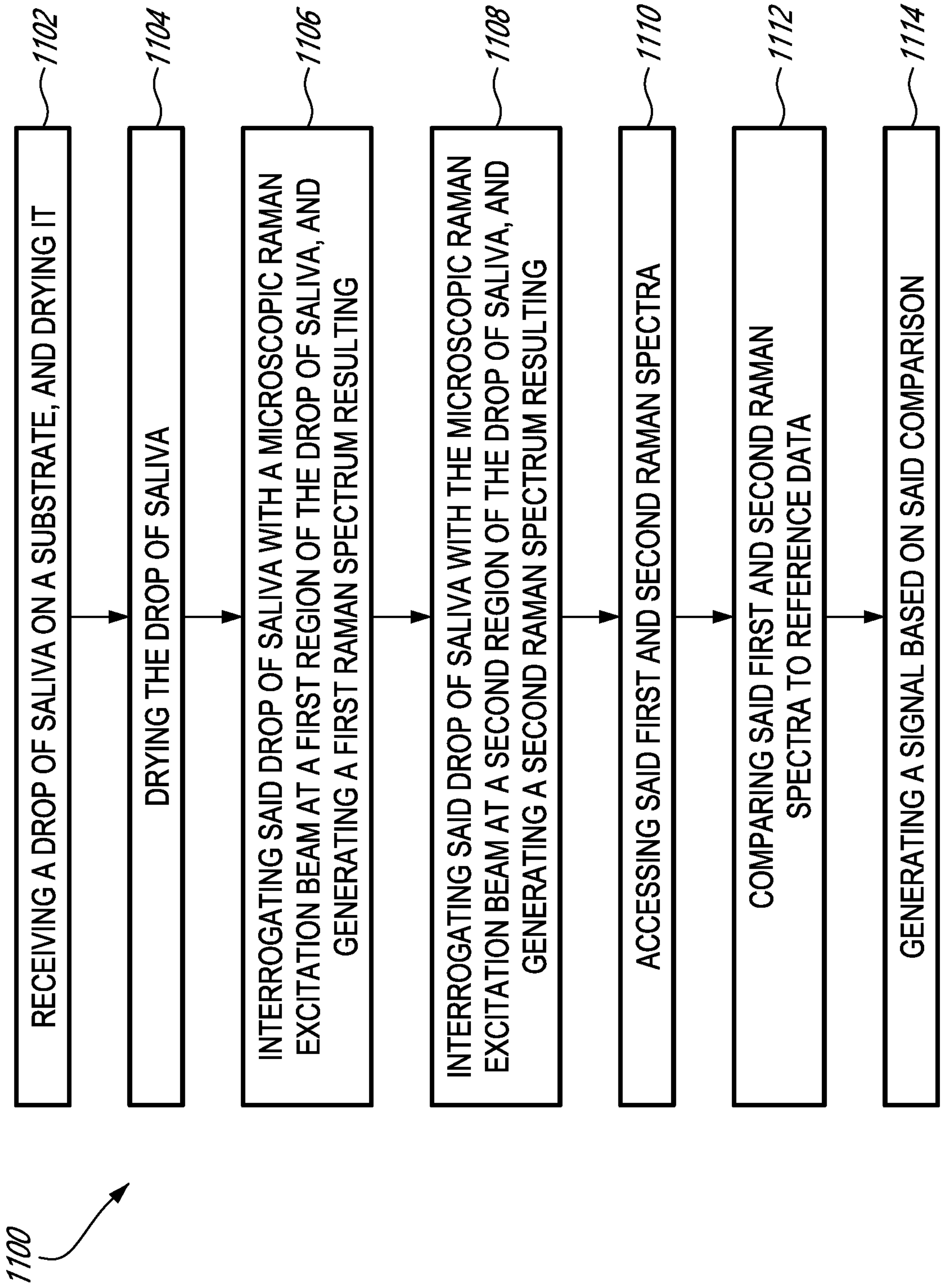
FIG. 11 is a flow chart of an example of a second method of interrogating saliva, involving a microscopic Raman excitation beam, in accordance with one or more embodiments.

FIG. 11 shows a flow chart of another example of a method of interrogating saliva.

As shown, at step 1102, a drop of saliva is received on a substrate. Although the substrate can be provided in the form of a well plate, it was found preferred to use a planar substrate. In some embodiments, the drop of saliva is provided in the form of a drop of saliva supernatant or a drop of saliva filtrate, depending on the embodiment. The volume of the drop generally ranges between about 0.5 μL and 100 μL, preferably between about 1 μL and 50 μL and most preferably between about 1 μL and 10 μL. Of course, the volume of the drop of saliva can, of course, vary from one embodiment to another.

At step 1104, the drop of saliva is dried to form a circular profile having a center region surrounded by an edge region, with crystalline elements and non-crystalline elements. The drying of the drop of saliva can be active or passive. More specifically, the drying can be accelerated using a heater creating heat, a blower blowing air onto the wet drop of saliva until it dries, or a combination of both depending on the embodiment. As the drying can be active, the drying can preferably be passive by letting the drop dry naturally under ambient air conditions.

At steps 1106 and 1108, first and second Raman spectroscopy measurements are performed on the drop of saliva. The first Raman spectroscopy measurement includes the interrogation of the drop of saliva with a Raman excitation beam focused on a first region of the drop of saliva, and the generation of a first Raman spectrum resulting from the first Raman spectroscopy measurement. The second Raman spectroscopy measurement includes the interrogation of drop of saliva with a Raman excitation beam focused on a second region of the dried drop of saliva, and the generation of a second Raman spectrum resulting from the first Raman spectroscopy measurement. The focused Raman excitation beam(s) typically have a dimension below a beam dimension threshold of about 50 μm, preferably below about 25 μm and most preferably below about 10 μm. The beam dimension threshold can range between about 1 μm and about 50 μm, preferably about 2 μm and about 25 μm, and most preferably about 5 μm and about 10 μm. To achieve such a beam dimension, a 50×, 25× or 10× microscope objective may be used as the focusing lens of the Raman excitation path. It is intended that the first and second regions are spaced apart from one another and contain different form and structure indicative of a different molecular content. In some instances, the first and second regions are visually different, which may be indicative of difference in their respective molecular content. For instance, the first region can encompass the center region of the dried drop of saliva whereas the second region can encompass the edge region of the dried drop of saliva. In some embodiments, the first region can encompass the crystalline elements of the dried drop of saliva whereas the second region can encompass the non-crystalline elements of the dried drop of saliva.

Depending on the embodiment and on the Raman spectroscopy measurement unit used, the first and second Raman spectroscopy measurements can be performed simultaneously or sequentially to one another.

At steps 1110, 1112 and 1114, a computer is used to access the first and second Raman spectra, compare the first and second Raman spectra to reference data, and generate a signal based on the comparison. In some embodiments, the reference data includes first and second reference Raman spectra associated to a medical condition and measured on corresponding first and second regions of the dried drop of saliva.

Figure 12:
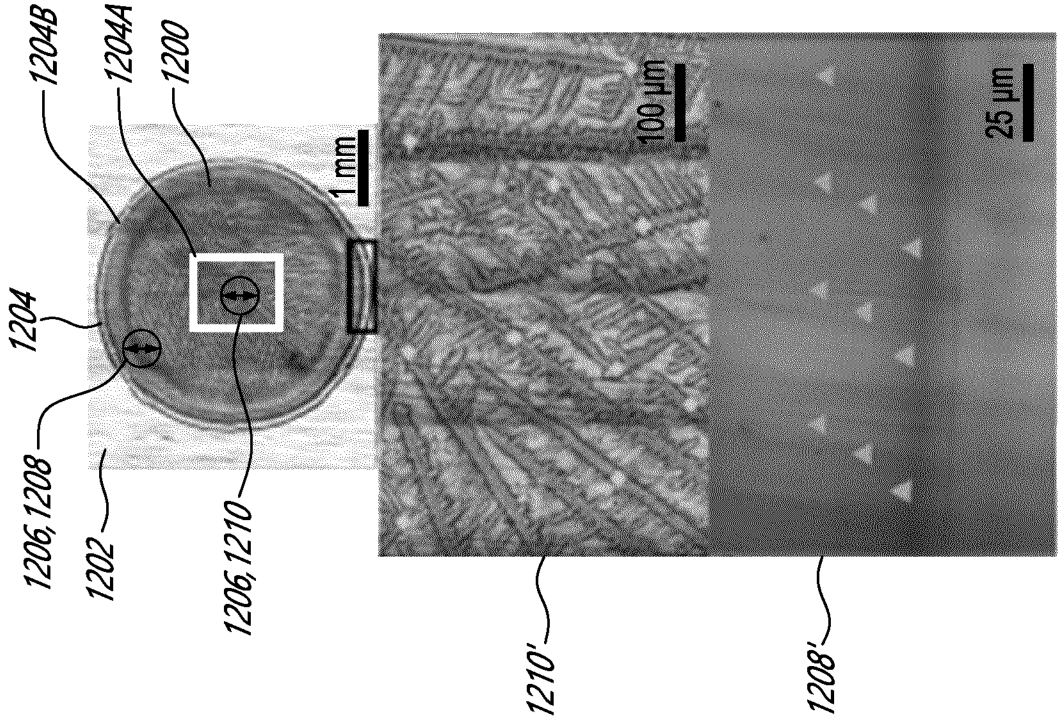
FIG. 12 is a top plan view of a dried drop of saliva received on a planar substrate, showing insets of crystalline and non-crystalline elements thereof, in accordance with one or more embodiments.
Figure 13:
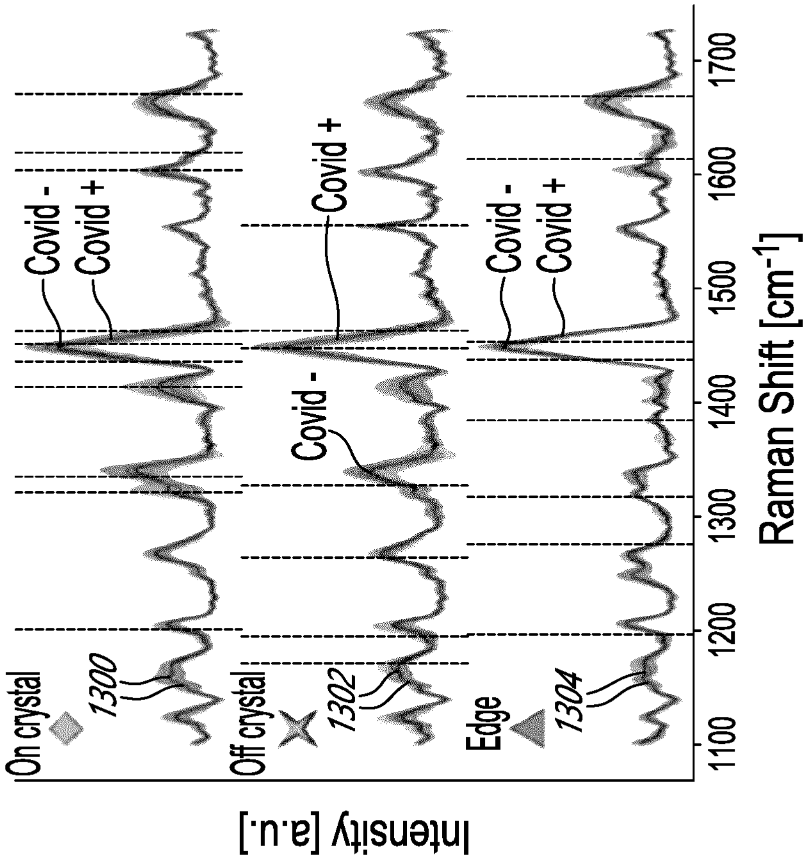
FIG. 13 is a graph showing an example of a Raman spectrum resulting from Raman spectroscopy measurements on the dried drop of saliva of FIG. 12, and corresponding reference Raman spectrum, in accordance with one or more embodiments.

FIG. 12 shows a top view of an example of a dried drop of saliva 1200 received onto a planar substrate 1202. As shown, the dried drop of saliva 1200 shows a circular profile 1204 exhibiting a center region 1204A surrounded by an edge region 1204B, with crystalline and non-crystalline elements. In this specific embodiment, a Raman excitation beam 1206 of the first Raman spectroscopy measurement is focused onto a first region 1208 encompassing at least a portion of the edge region 1204B, with non-crystalline elements. The Raman excitation beam of the second Raman spectroscopy measurement is focused onto a second region 1210 encompassing at least a portion of the center region 1204A, with crystalline elements. Inset 1208' shows an enlarged view of the non-crystalline elements of the edge region 1204B of the drop of saliva 1200 whereas inset 1210' shows an enlarged view of the crystalline elements of the center region 1204A of the dried drop of saliva 1200. It was found that by capturing the Raman emission content stemming from such morphologically different molecular content, the medical condition assessment can be more apparent upon comparison with corresponding reference data. FIG. 13 shows examples of Raman spectra 1300 acquired onto the crystalline elements of the center region 1204A for COVID-19 positive and COVID-19 negative drops of saliva, examples of Raman spectra 1302 acquired onto the non-crystalline elements of the center region 1204A for COVID-19 positive and COVID-19 negative drops of saliva, and examples of Raman spectra 1304 acquired onto the non-crystalline elements of the edge region 1204B for COVID-19 positive and COVID-19 negative drops of saliva. As shown, by comparing these Raman spectra to corresponding reference Raman spectra, a medical condition may be assessed.

As can be understood, the examples described above and illustrated are intended to be exemplary only. The scope is indicated by the appended claims.

What is claimed is:

1. A method of interrogating saliva, the method comprising:

receiving a drop of saliva on a substrate, the substrate made of a material which is not or less susceptible to Raman emission upon Raman excitation;

using a spontaneous Raman spectroscopy measurement unit, performing a spontaneous Raman spectroscopy measurement on the drop of saliva received on the substrate, said performing including interrogating said drop of saliva with a Raman excitation beam having a beam dimension greater than a given beam dimension threshold of about 0.1 mm, thereby simultaneously interrogating molecular content distributed in at least a given area of the drop of saliva, and generating at least a Raman spectrum resulting from said spontaneous Raman spectroscopy measurement; and using a computer, accessing said Raman spectrum, comparing said Raman spectrum to reference data, and generating a signal based on said comparison.

2. The method of claim 1 wherein the substrate has a well, said receiving including receiving the drop of saliva within the well, the well having a floor surface and an internal wall surface protruding from said floor surface, the floor surface and at least a portion of the internal wall surface confining the drop of saliva therewithin, the confined drop of saliva having molecular content being homogeneously distributed across the well.

3. The method of claim 2 wherein said performing includes interrogating at least a portion of the homogeneously distributed molecular content of the confined drop of saliva confined within the well.

4. The method of claim 2 wherein said receiving includes drying the drop of saliva.

5. The method of claim 4 wherein said performing includes simultaneously interrogating at least some of the crystalline elements and at least some of the non-crystalline elements of the dried drop of saliva received on the planar substrate.

6. The method of claim 1 wherein said substrate is a planar substrate, said receiving including depositing a drop of saliva on the planar substrate.

7. The method of claim 6 further comprising drying the drop of saliva deposited on the planar substrate, the drop of saliva drying into a circular profile having a center region surrounded by an edge region, with crystalline elements and non-crystalline elements.

8. The method of claim 1 wherein the beam dimension threshold is between about 0.1 mm and about 10 mm.

9. The method of claim 1 wherein the Raman excitation beam simultaneously encompasses at least a portion of a center region and at least a portion of an edge region of the drop of saliva.

10. The method of claim 1 wherein said reference data includes a reference Raman spectrum associated to a medical condition, said comparing including comparing the Raman spectrum to the reference Raman spectrum, and determining whether the medical condition is present in the drop of saliva based on said comparing.

11. The method of claim 10 wherein said comparing includes comparing Raman emission content present within a given spectral region of the Raman spectrum to reference Raman emission content present within the given spectral region of the reference Raman spectrum.

12. The method of claim 11 wherein said medical condition is COVID-19 positive, the given spectral region extends between about 300 $cm^{-1}$ and about 3500 $cm^{-1}$.

13. The method of claim 1 wherein the drop of saliva has a volume ranging between about 0.5 μl and 100 μL.

14. The method of claim 1 wherein the substrate is non-metallic.

15. A spontaneous Raman spectroscopy system for interrogating saliva, the Raman spectroscopy system comprising:

a substrate receiving a drop of saliva, the substrate made of a material which is not or less susceptible to Raman emission upon Raman excitation;

a spontaneous Raman spectroscopy measurement unit configured for performing a spontaneous Raman spectroscopy measurement on the drop of saliva received on the substrate, said performing including interrogating said drop of saliva with a Raman excitation beam having a beam dimension greater than a given beam dimension threshold of about 0.1 mm, thereby simultaneously interrogating molecular content distributed in at least a given area of the drop of saliva, and generating at least a Raman spectrum resulting from said spontaneous Raman spectroscopy measurement; and a computer communicatively coupled to the spontaneous Raman spectroscopy measurement unit, the computer having a processor and a memory having stored thereon instructions that when executed by the processor perform the steps of:

accessing said Raman spectrum;

comparing said Raman spectrum to reference data; and generating a signal based on said comparison.

16. The spontaneous Raman spectroscopy system of claim 15 wherein the beam dimension threshold is between about 0.1 mm and about 10 mm.

17. The spontaneous Raman spectroscopy system of claim 16 wherein the substrate has a well, the well having a floor surface and an internal wall surface protruding from said floor surface, the floor surface and at least a portion of the internal wall surface confining the drop of saliva therein, the confined drop of saliva having molecular content being homogeneously distributed across the well.

18. The spontaneous Raman spectroscopy system of claim 17 wherein the well has a cross-sectional area smaller than 80 $mm^2$, and wherein the well has a depth below about 100 mm.

19. The spontaneous Raman spectroscopy system of claim 15 wherein the substrate is non-metallic.

20. The spontaneous Raman spectroscopy system of claim 15 wherein said substrate is a planar substrate.

* * * * *